United States Patent
Tuurenhout et al.

(10) Patent No.: US 6,231,741 B1
(45) Date of Patent: May 15, 2001

(54) GEL CASSETTE AND ELECTROPHORESIS DEVICE

(75) Inventors: Matthijs W. F. Tuurenhout, Leiderdrop; Paul Venema, Leiden; Gerrit J. De Vos, Tulpstraat 15, NL-4486 BX, Colijnsplant, all of (NL)

(73) Assignee: Gerrit J. de Vos, Leimuiden (NL)

( * ) Notice: Subject to any disclaimer, the term of this patent is extended or adjusted under 35 U.S.C. 154(b) by 0 days.

(21) Appl. No.: 08/809,813

(22) PCT Filed: Sep. 29, 1995

(86) PCT No.: PCT/NL95/00328

§ 371 Date: Sep. 30, 1997

§ 102(e) Date: Sep. 30, 1997

(87) PCT Pub. No.: WO96/10743

PCT Pub. Date: Apr. 11, 1996

(Under 37 CFR 1.47)

(30) Foreign Application Priority Data

Mar. 30, 1994 (NL) .................................................. 9401611
Mar. 3, 1995 (NL) .................................................. 9500431

(51) Int. Cl.[7] .................................................. G01N 27/26
(52) U.S. Cl. .......................................... 204/618; 204/619
(58) Field of Search ................................... 204/606, 615, 204/616, 617, 618, 619, 607; 428/47, 122; 249/187.1

(56) References Cited

U.S. PATENT DOCUMENTS

| | | | | |
|---|---|---|---|---|
| 1,634,878 | * | 7/1927 | McKinney | 428/122 |
| 3,563,872 | * | 2/1971 | Huebner | 204/520 |
| 3,969,218 | * | 7/1976 | Scott | 204/613 |
| 4,035,377 | * | 7/1977 | Detroy | 204/619 |
| 4,560,459 | * | 12/1985 | Hoefer | 204/467 |
| 4,612,106 | * | 9/1986 | Kromer et al. | 204/618 |

(List continued on next page.)

FOREIGN PATENT DOCUMENTS

3931851 * 4/1991 (DE).
224194 * 6/1987 (EP).

OTHER PUBLICATIONS

Caplus abstract of Thormann et al. ("Detection of transient and steady states in electrophoresis: description and applications of a new apparatus with 255 potential gradient detectors along the separation trough", Electrophoresis (1984), 5(6), 323–37), Jul. 1984.*

Brown et al, ("A modificatiton for 'smileless' polyacrylamide gels in nucleic acid sequencing", Electrophoresis (1986), 7(1), 54–5, Jul. 1986.*

Patent abstract of JP61007458 (Hitachi Seisakusho K.), Jan. 1986.*

Primary Examiner—Jill Warden
Assistant Examiner—Alex Noguerola
(74) Attorney, Agent, or Firm—Banner & Witcoff, Ltd.

(57) ABSTRACT

The invention relates to a gel cassette, comprising two glass plates and a substantially H- or U-shaped spacer. One of the two glass plates is preferably provided with sensors for measuring at least one gel parameter, such as the potential or the temperature. The spacer consists for instance of two part placed vertically in the situation of use which are mutually connected by means of a part lying substantially perpendicular thereto and substantially horizontal in the situation of use, wherein the horizontal part is provided with teeth. The invention further relates to the spacer, a glass plate for use in an electrophoresis cassette provided with sensors for measuring one or more gel parameters, an electrohporesis apparatus comprising a buffer container consisting of an upper buffer compartment and a lower buffer compartment, power points for applying a voltage between the upper buffer compartment and the lower buffer compartment and integral means for flushing a remaining space between the glass plates under the gel, and an assembly of a gel cassette and an electrophoresis apparatus according to the invention.

25 Claims, 12 Drawing Sheets

U.S. PATENT DOCUMENTS

| | | | | |
|---|---|---|---|---|
| 4,772,373 | * | 9/1988 | Ebata et al. | 204/618 |
| 4,820,398 | * | 4/1989 | Yamamoto | 204/618 |
| 5,106,477 | * | 4/1992 | Coleman | 204/299 R |
| 5,112,736 | * | 5/1992 | Caldwell et al. | 435/6 |
| 5,192,408 | * | 3/1993 | Scott | 264/219 |
| 5,232,573 | * | 8/1993 | Rosenvold | 204/299 R |
| 5,284,559 | * | 2/1994 | Lim et al. | 204/461 |
| 5,324,412 | * | 6/1994 | Kolner | 204/299 R |
| 5,328,581 | * | 7/1994 | Sorge | 204/457 |

* cited by examiner

GEL CASSETTE AND ELECTROPHORESIS DEVICE

The present invention relates to a gel cassette and an electrophoresis apparatus to be used therewith.

The separation of different biological materials, such as proteins, RNA and DNA generally takes place by means of electrophoresis. This technique is based on the measurement of the mobility of molecules in an electrical field. The migration speed of a molecule in an electrical field depends on the electrical field strength, the net electric charge on the molecule and the frictional resistance. When a detergent such as sodium dodecyl sulphate (SDS) is added to the gel, the separation is only based on differences in size.

An electrophoretic separation takes place in a gel, for instance an agarose gel or a polyacrylamide gel. Particularly these latter gels are very thin and are manufactured by causing a still liquid polyacrylamide solution to polymerize between two glass plates. The thickness of the gel is determined by the so-called spacers, which are situated between the glass plates.

Because the starting point is a gel solution which in the first instance is liquid, the space between the glass plates must be a leak-free compartment, since otherwise the gel solution would immediately run out again from between the glass plates. A gel cassette consists for this purpose of two glass plates, two side spacers and a plug which closes off the underside of the space. The spacers on the side parts of the gel have a dual function, on the one hand in defining the casting compartment and on the other hand for an electrical insulation of the gel between the glass plates relative to the buffer outside the glass plates.

The underside of the glass plates is closed off before casting the gel. Use can be made herein for instance of an agarose plug or a polyacrylamide plug. The advantage hereof is that the gel cassette consisting of the glass plates and the side spacers can be mounted directly into the electrophoresis apparatus and can also remain there. The great drawback however is that casting of a gel in this manner takes a great deal of time. In addition, the agarose plug has the drawback that the electrophoresis process can be slowed thereby.

It is further also possible to arrange a sealing profile on the underside of the gel cassette, wherein leakage of the liquid gel solution from between the glass plates is prevented by means of clamps. The use of tape for sealing is often also necessary herein. Even then, however, a leak-free cassette is not always obtained. This method of working moreover has the drawback that arrangement and removal of the tape require extra operations. Furthermore, the gel cassette can only be placed in the electrophoresis apparatus after polymerization of the gel, because the sealing profile, the clamps and the optional sealing tape can be removed prior to electrophoresis but only after polymerization of the gel.

The present invention has for its object inter alia to provide a gel cassette and electrophoresis apparatus with which the above mentioned drawbacks can be obviated and with which it is optionally also possible to determine whether the buffer still functions properly.

The invention provides for this purpose a gel cassette, comprising two glass plates with a substantially H- or U-shaped spacer for placing therebetween. When a substantially H- or U-shaped spacer is used, both sides and the underside of the space between the glass plates are sealed by the spacer during casting. The two vertical side parts of the spacer preferably protrude above the glass plate. After polymerization of the gel solution between the glass plates, the vertical parts of the spacer are pushed downward, whereby the spacer will drop and the underside of the gel will be released. Hereby occurs the required electrical contact between the underside of the gel and the surrounding buffer. The side of the gel continues to remain isolated from the buffer by the spacer. Underneath the gel there remains a small space between the glass plates where no gel is present.

Using the gel cassette according to the invention it is possible to create rapidly a leak-free space between glass plates, into which the gel can be cast.

In an alternative embodiment the invention provides a gel cassette which can be used to cast so-called perpendicular gels. These are gels in which the gradient runs not in vertical but in horizontal direction. For this purpose at least one of the parts of the spacer placed vertically in the situation of use consists of two portions mutually connecting in liquid-tight manner to define a passage opening for gel solution. For casting of the gel, the gel cassette is rotated a quarter-turn, whereby the divided part of the spacer is situated at the top. By pushing apart the two parts a passage opening is formed, through which the space defined by the spacer and the glass plates can be filled with gel solution. After polymerization the gel cassette can be placed upright again and electrophoresis can take place.

When a comb with two wide teeth is used, two gels can be run simultaneously. During casting one gradient gel is cast first, whereafter a narrow segment of gel without gradient is arranged in order to separate the two gradient gels from each other. The second gel can then be cast.

The ends of the two portions of the vertical spacer part which connect mutually in liquid-tight manner are preferably toothed but mutually fitting concave and convex or step profiles are also possible. The advantage of a toothing is that the mutually abutting positioning of the two portions then proceeds easily.

To ensure a good sealing at the position of the comb which functions as a side during casting of the gel, the invention provides as extra accessory with the gel cassette a pressure clamp comprising a U-shaped element and a pressure element protruding through one of the legs thereof. In order to fix the pressure clamp a recess can be incorporated in the U-shaped element for passage of the hose pillar of the buffer container. The pressure element is for instance a screw which can be provided with a plate on the end remote from the head.

The combination of the divisible spacer and the pressure clamp forms an adapter set for casting perpendicular gels. The adapter set can be used with any desired cassette.

Because a gel shrinks slightly after polymerization it will no longer be connected to the side parts of the spacer. No samples can therefore be arranged on the edge of the gel because due to the space between the gel and the spacer variations may occur in the gradient and the electrical field and therefore in the band pattern. In order to prevent this the parts of the spacer substantially vertical in the situation of use are wider on their end remote from the part of the gel substantially horizontal in the situation of use. In practice this means that in the case of a spacer which is pressed downward the upper sides of the vertical spacer parts are wider, while in the case of a spacer which is pulled upward, such as a spacer with comb, it is on the contrary the lower ends of the vertical parts which are wider. The outward facing edge of these vertical parts preferably runs straight, while the inward facing edge can taper toward the outer end in a convex, concave or linear manner.

During casting of the gel air bubbles can develop at the bottom, which are difficult to remove and can cause malfunction of the gel. To prevent this the spacer is preferably provided with a shoulder at the position of the connection of the horizontal part onto the vertical part. By tilting the gel cassette the air bubble will rise along the horizontal part of the spacer in the direction of the vertical part of the shoulder. Having arrived there it will move along that vertical shoulder part and finally along the horizontal shoulder part to ultimately come to a stop against the vertical spacer part. When the gel cassette is placed upright again the air bubble will no longer be able to return to the bottom of the gel, since that would be a downward movement which will never be made by an air bubble. The air bubble can possibly rise along the vertical spacer part or remain in the corner between the vertical spacer part and the horizontal shoulder part. In this position the air bubble no longer has any effect on the electrophoresis.

In another preferred embodiment of the invention the horizontal part of the spacer takes the form of a comb. When such a spacer is used the gel is cast upside down. When after polymerization of the gel the spacer is pushed slightly to what is normally the upper side of the gel, the teeth of the comb will leave so-called slots in the gel, into which the sample for electrophoresis can be placed. Because the gel is cast upside down, such a spacer with built-in comb cannot be used in gradient gels, where the heaviest solution has to be situated at the bottom of the gel. In casting this is the upper part of the gel.

The advantage of a gel cassette wherein the spacer contains a built-in comb is that because the gel is cast upside down on the underside thereof, no gap remains between the glass plates where no gel is present.

A possible problem of this gap remaining after the spacer is moved is that gas, in most cases oxygen, can accumulate. Such a gas accumulation can make the electrophoresis more difficult or cause distorted electrophoresis patterns.

According to the invention an electrophoresis apparatus is therefore further provided, comprising a buffer container consisting of an upper buffer compartment and a lower buffer compartment, power points for applying a voltage between the upper buffer compartment and a lower buffer compartment and integral means for flushing of the remaining space between the glass plates under the gel, for instance in the form of a conduit with a plurality of outlet openings at the position of the space through which buffer liquid can be guided.

In order to obtain optimal flushing one of the two glass plates is preferably made slightly longer, so that this glass plate protrudes slightly on the underside of the gel cassette.

With the means for flushing the space remaining between the glass plates and the gel according to the invention, in addition to the removal of the air bubbles accumulating therein, a possibility is also provided for flushing the buffer space.

During electrophoresis an electrical field is applied over the gel on which the sample for testing, for instance DNA, is loaded. The components of the sample migrate through the gel under the influence of the electrical field. Depending on their size and/or charge they will migrate further or less far. Used as intermediary between the gel and the electrodes which provide the electrical field is an electrophoresis buffer. The electrophoresis buffer is an electrically conducting salt solution with a buffering activity. The buffering activity is necessary because the migration behaviour of the sample is strongly influenced by the degree of acidity of the environment. If the salt solution had no buffering activity the degree of acidity of the environment would vary greatly through the occurrence of electrode reactions. The most important of these is the electrolysis of water, whereby hydrogen is formed on the cathode and oxygen on the anode. The pH on the cathode will thereby fall and that of the anode will rise. By neutralizing these alkaline and acid groups the buffer prevents charged alkaline and acid groups migrating into the gel and there changing the pH. After a period of time however the buffering activity of the salt solution is exhausted.

By flushing the space under the gel between the glass plates, not only is the removal of air bubbles ensured but also that exhaustion of the buffer and deformation of the electrical field are reduced or even prevented. Such a flushing is of course also useful in this respect in the case of gels wherein there is no gap between the glass plates.

When the electrophoresis buffer is used more than once it can also become exhausted to such an extent that simple flushing of the buffer container is no longer sufficient. It is therefore very desirable to be able to determine whether the buffering activity of the salt solution is still sufficient.

For this purpose the invention further provides an electrophoresis apparatus which is provided with means for measuring the electrical conductance of the buffer and/or the effective electrical field strength in the gel and means for indicating whether or not the buffer is exhausted.

Due to the activity of the buffer the chemical composition thereof will also change. This is reflected in the electrical conductance of the buffer. A new buffer will have a higher electrical conductance than one which has already been used a number of times. By relating the electrical conductance to the buffer quality a criterion is obtained on the basis of which can be determined when the buffer needs replacing.

In a particularly advantageous embodiment of the invention the electrical conductance of the buffer is determined by means of a so-called alternating current bridge. This is a per se known technique for determining unknown complex impedances. The alternating current bridge has however not been used before to determine the electrical conductance of an electrophoresis buffer. In this embodiment the bridge is placed in the buffer tank.

In an alternative embodiment of the invention the conductance measurement is performed over the electrodes. In this case the effective electrical field strength can also be determined. The effective electrical field prevailing in the gel is one of the quantities which codetermines the speed of the electrophoresis. The field strength in the gel will not be the same as the externally applied electrical field because so-called polarization charges are formed on the electrodes in the form of salt ions. The polarization charges will partly shield the externally applied field, whereby the field in the gel is smaller than the external field. When an alternating current bridge is now connected over the electrodes both the resistance and the capacity can be determined. The first quantity is a measure for the buffer quality, and with the second the effective electrical field prevailing inside the gel can be measured.

The apparatus can further comprise indicator means coupled to the determining means which indicate when the buffer is exhausted and/or what the effective field strength is. As indicator means can be used for instance one or more lamps optionally changing colour, or a display, which may or may not be digital.

An alternative embodiment of the electrophoresis apparatus comprises the means for preventing gas accumulation which are formed by a recess situated in the bottom of the lower buffer compartment for partly receiving therein a gel cassette, which recess defines a space underneath the gel cassette placed in the apparatus, which space is in contact with the lower buffer compartment via a passage under the glass plate. A recess is preferably provided in the bottom of the space for receiving therein of the spacer. Due to this construction air bubbles, which only rise and will never move downward in a liquid, cannot reach the space under the gel via the passage beneath the glass plate. Gas accumulation is thereby prevented.

In principle any suitable material can be used for manufacture of the spacer. However, it must preferably comply with a number of conditions. It must be capable of closing liquid-tightly the space between the glass plates during casting of the gel. It must moreover be capable of electrically insulating the gel properly from the buffer in the environment. In addition, the material has to be so smooth that it can easily slide between the glass plates, this in respect of the movement of the spacer after polymerizing of the gel. The material must furthermore be so firm that the underside does not begin to bulge during displacement of the spacer between the glass plates, whereby the middle of the spacer could be left behind on the underside between the glass plates. A particular preference is given to teflon. The comb is preferably manufactured from teflon from a roll. The advantage hereof is that the material is somewhat curved, whereby the comb can be placed more easily between the glass plates. It is also possible to combine different materials. The invention likewise relates to the spacer as a separate component.

The horizontal part of the spacer can be provided with teeth directed to the gel. This prevents the creation of a vacuum under the gel when the spacer is pushed down. The gel could be damaged by the occurrence of a vacuum.

In a preferred embodiment of the gel cassette according to the invention at least one of the two glass plates is provided with at least one measuring point of an electrically conducting material which is in contact with the gel. The electrically conducting material is attached on its other end to a measuring wire. Using these measuring points the equipotential lines, and thereby the electrical lines of flux running perpendicular thereto, can be determined. The measuring points are preferably distributed evenly over the glass plate. Platinum for instance can be used as electrically conducting material. In principle such a glass plate can also be used in a conventional gel cassette. It is likewise possible to include different types of measuring point in one glass plate. The invention therefore also relates to a glass plate provided with measuring points as a separate component.

In this embodiment the electrophoresis apparatus according to the invention is augmented with means connected to the measuring points for measuring the potential.

When the number of measuring points is increased such that the spatial resolution of the gel is approached and the reproducibility and sensitivity are great enough, the passage of a DNA fragment can be detected by determining the disturbance in the electrical field.

In an alternative embodiment of such a detection glass plate, temperature-dependent resistances or other temperature-sensitive components with which the temperature in the gel can be determined can be used instead of electrically conducting material.

The electrophoresis apparatus according to the invention is augmented in this alternative embodiment with means for measuring the temperature which are connected to the measuring points.

Analogously with the above, any desired detection means can of course be incorporated in one or both glass plates to determine a desired parameter in the gel.

The present invention will be further elucidated with reference to the accompanying drawings in which corresponding reference numerals refer to corresponding components and in which.

Figure 1:
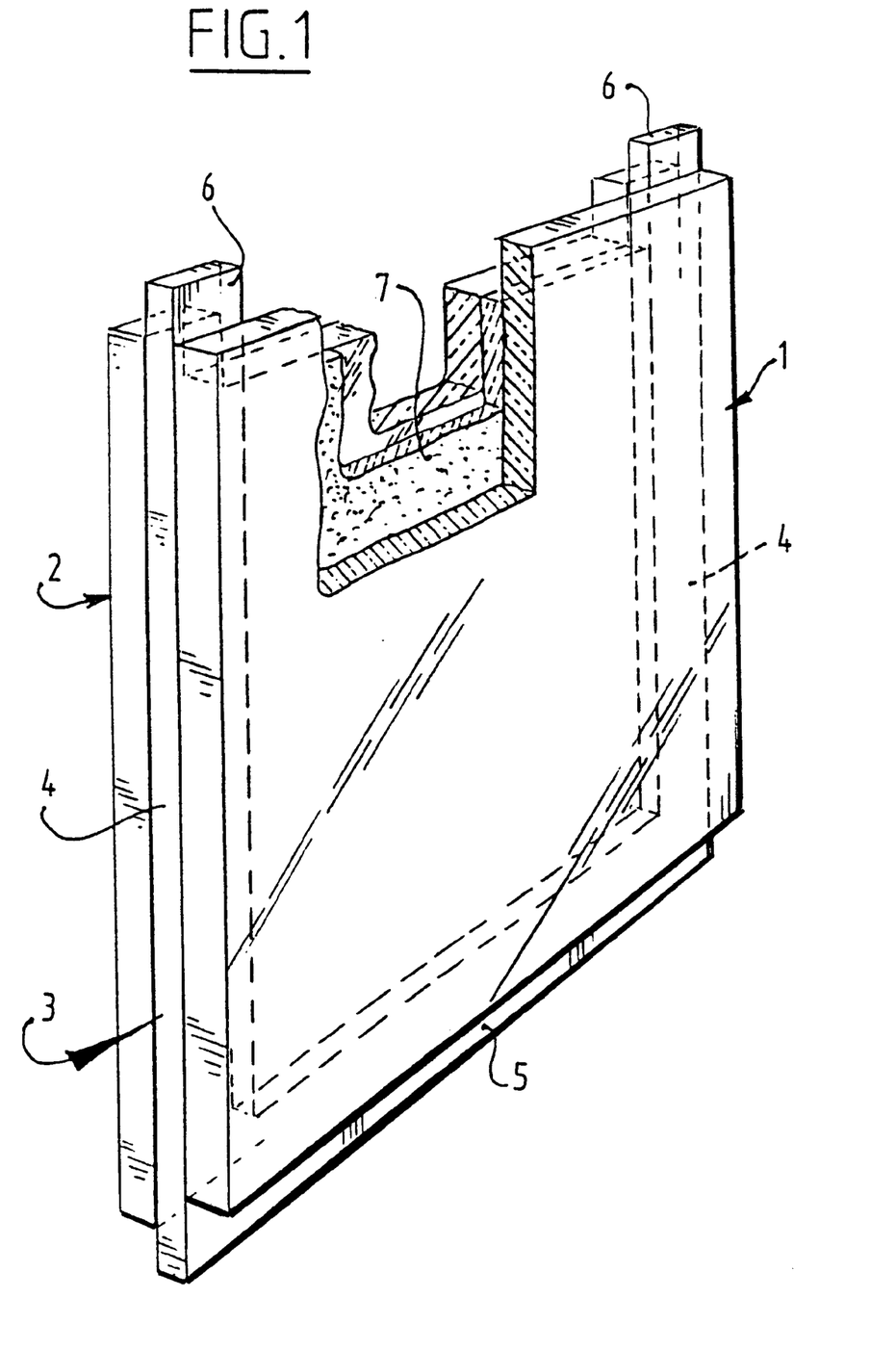
FIG. 1 shows a partly broken away perspective view of a gel cassette according to the invention.

FIG. 1 shows two glass plates 1 and 2, wherein the top part of glass plate 2 is partly lowered to facilitate placing of the samples on the gel. A spacer 3 is placed between the glass plates. The spacer consists of vertical side parts 4 and a horizontal part 5. Glass plate 2 is slightly longer at the bottom than glass plate 1. The spacer is placed between the glass plates such that it has two protruding portions 6 on its upper side. In the space which is defined by the two glass plates and the spacer is situated the gel 7.

Figure 2:
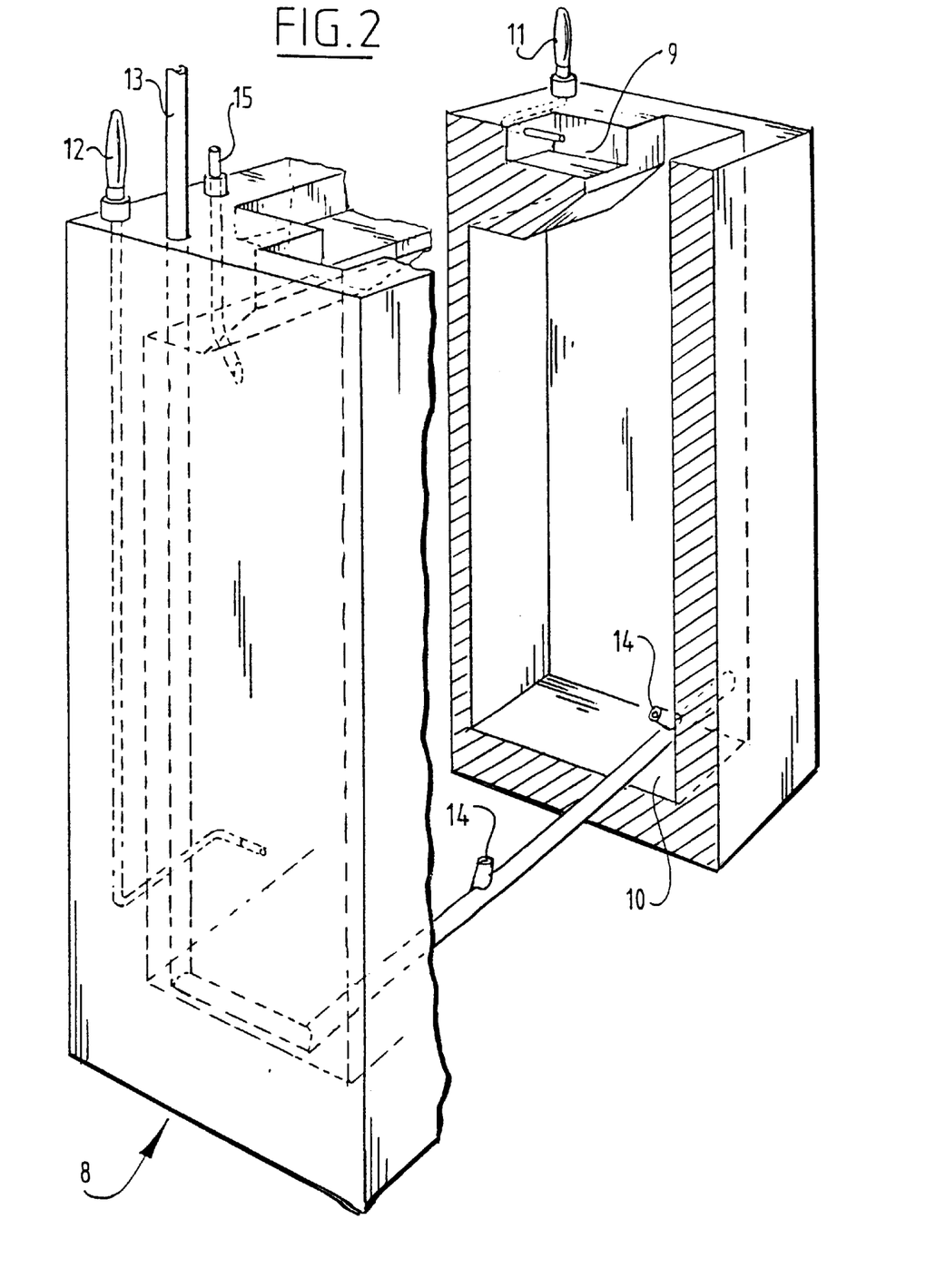
FIG. 2 shows a partly broken away perspective view of an electrophoresis apparatus according to the invention.

FIG. 2 shows an electrophoresis apparatus consisting of a buffer container 8 in which two buffer compartments 9 respectively 10 are situated. The apparatus further shows connecting pins 11 and 12 for applying a voltage therebetween. When the gel is placed in the apparatus, the circuit will be closed and the current will run from the upper compartment via the gel to the lower compartment. In the buffer container 8 runs a flushing conduit 13 provided with two outlet openings 14 to flush away air bubbles in the space between glass plates 1 and 2 beneath the gel 7 and to keep the electrophoresis buffer moving in order to prevent exhaustion thereof.

Figure 3:
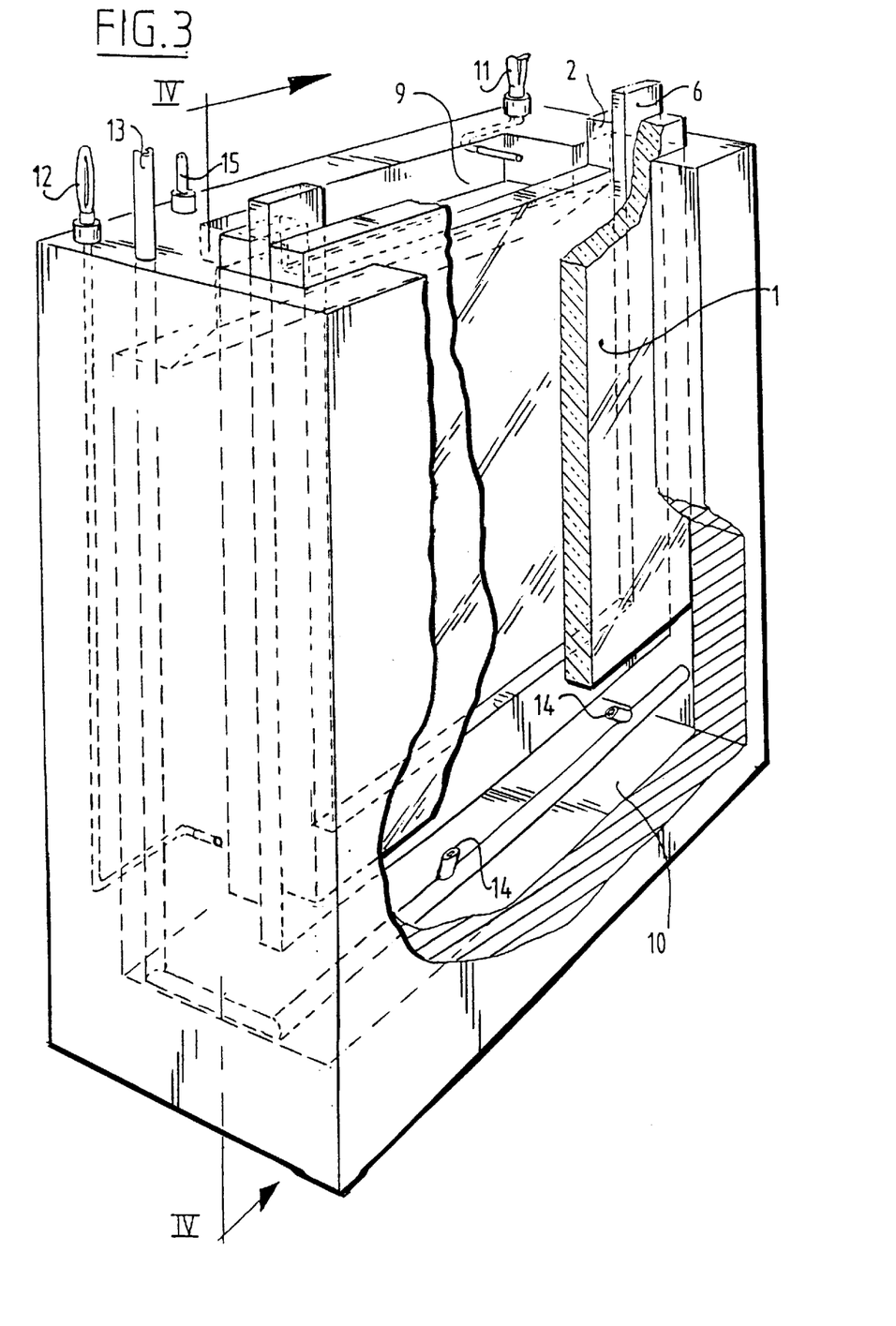
FIG. 3 shows a partly broken away perspective view of an electrophoresis apparatus according to the invention with gel cassette placed therein.

The placing of the gel cassette in the electrophoresis apparatus can be seen in FIG. 3. The upper compartment 9 is in contact with the gel via the lowered portion of the top part of glass plate 2. The lower part of the gel is in contact with the buffer in the lower buffer compartment 10. In the arrangement shown in FIG. 3 the spacer has not yet been pushed downward. There is therefore no contact yet between the gel and the buffer in the lower compartment 10.

Figure 4:
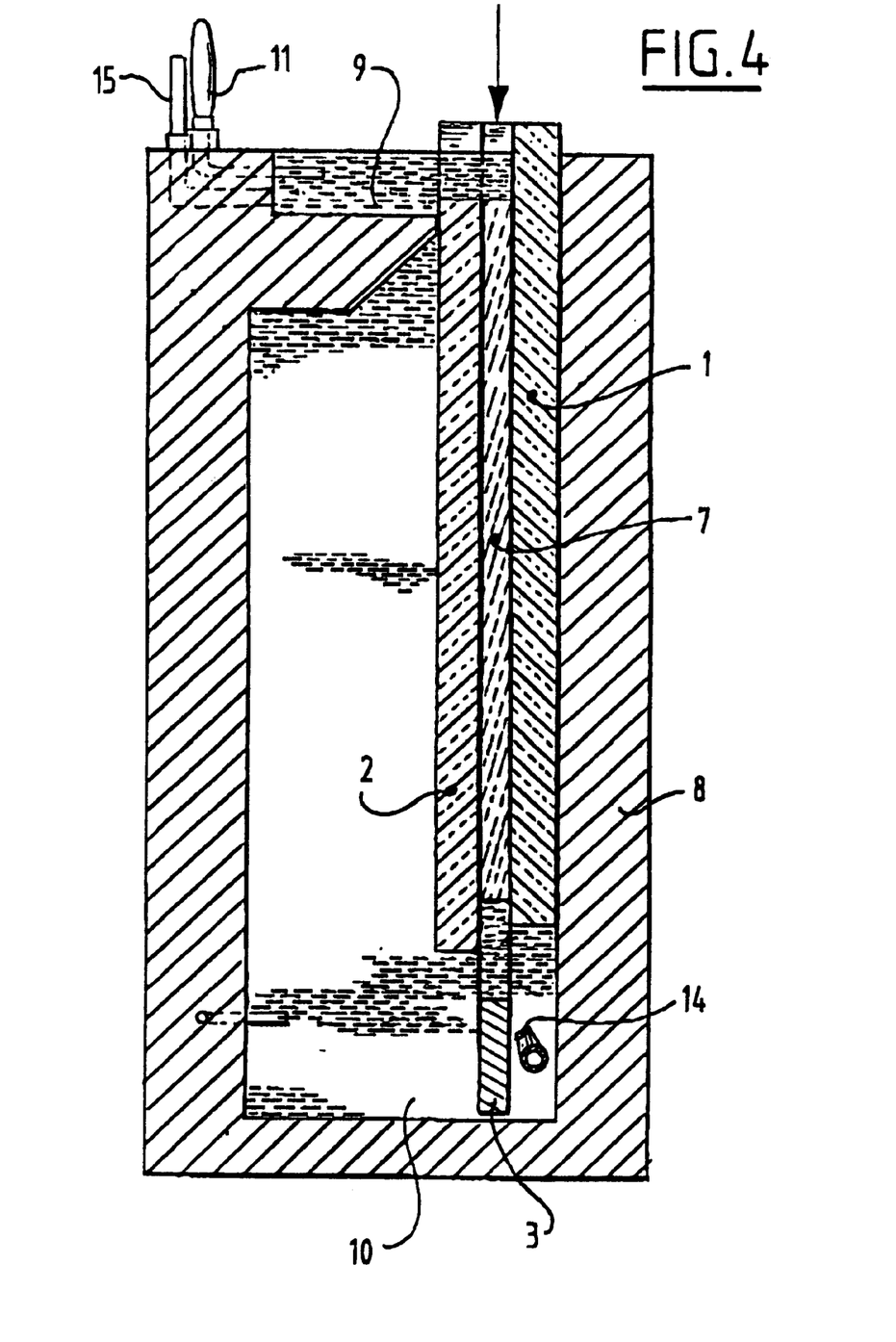
FIG. 4 shows a cross-sectional view according to the line IV—IV in FIG. 3.

FIG. 4 shows a cross-section wherein the spacer has been pushed downward whereby the buffer from buffer compartment 10 is in contact with the lower part of the gel 7. The circuit is now closed when, via connecting points 11 and 12, a voltage is applied between the two buffer compartments 9 and 10. The outlet opening 14 ensures that air bubbles in the gap between glass plates 1 and 2 under the gel 7 are flushed away.

The upper buffer compartment 9 can be flushed using the so-called hose pillar 15.

Figure 5:
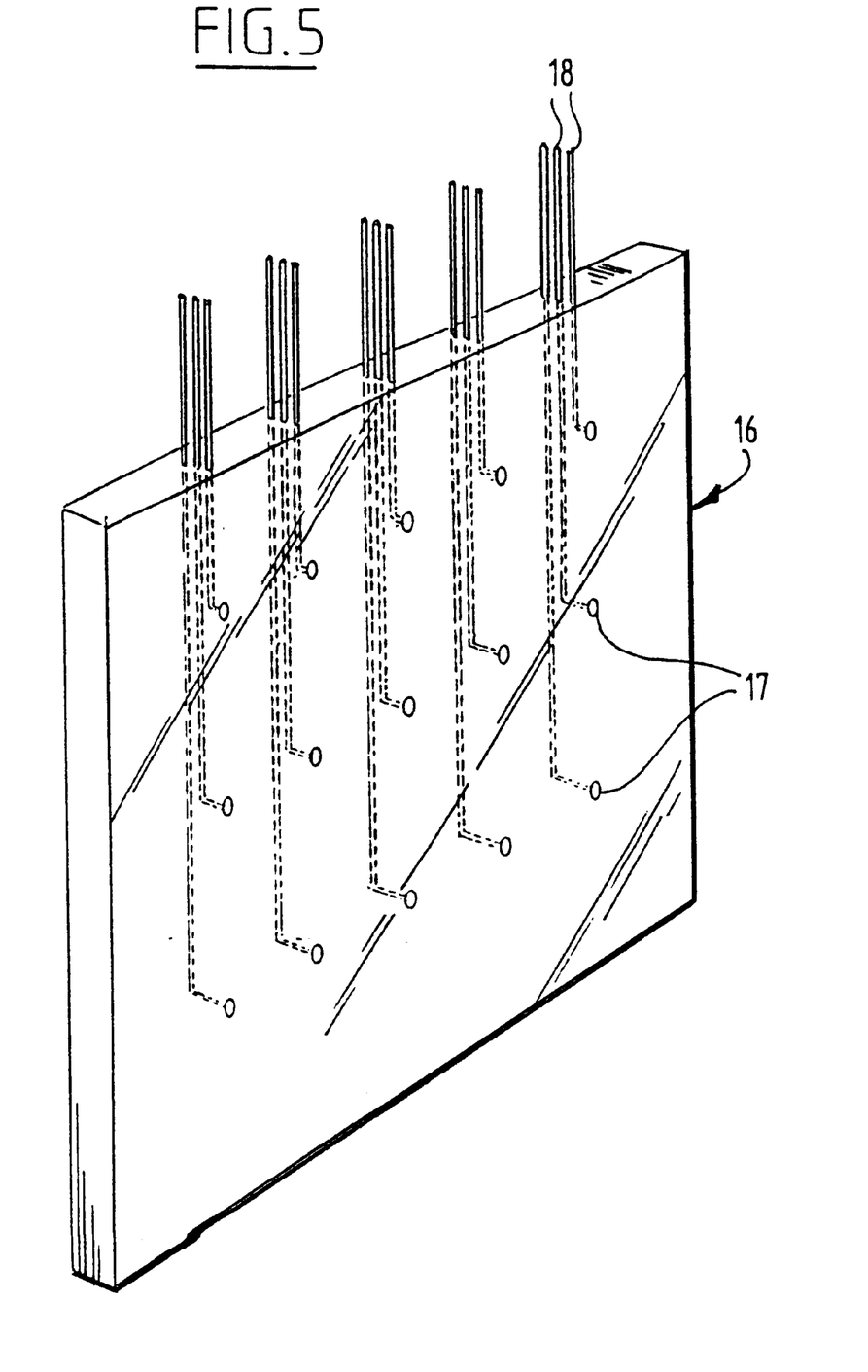
FIG. 5 shows a partly broken away perspective view of a glass plate with sensors.

FIG. 5 shows a glass plate 16 provided with a large number of measuring points 17 which are connected to measuring wires 18. Different measurements can be performed at the measuring points, depending on the nature of the measuring point. Measurement of the potential in the gel or measurement of the temperature can be envisaged here. In the first case the measuring point consists for instance of electrically conducting material. In the other case temperature-sensitive resistances can for instance be used.

Figure 6:
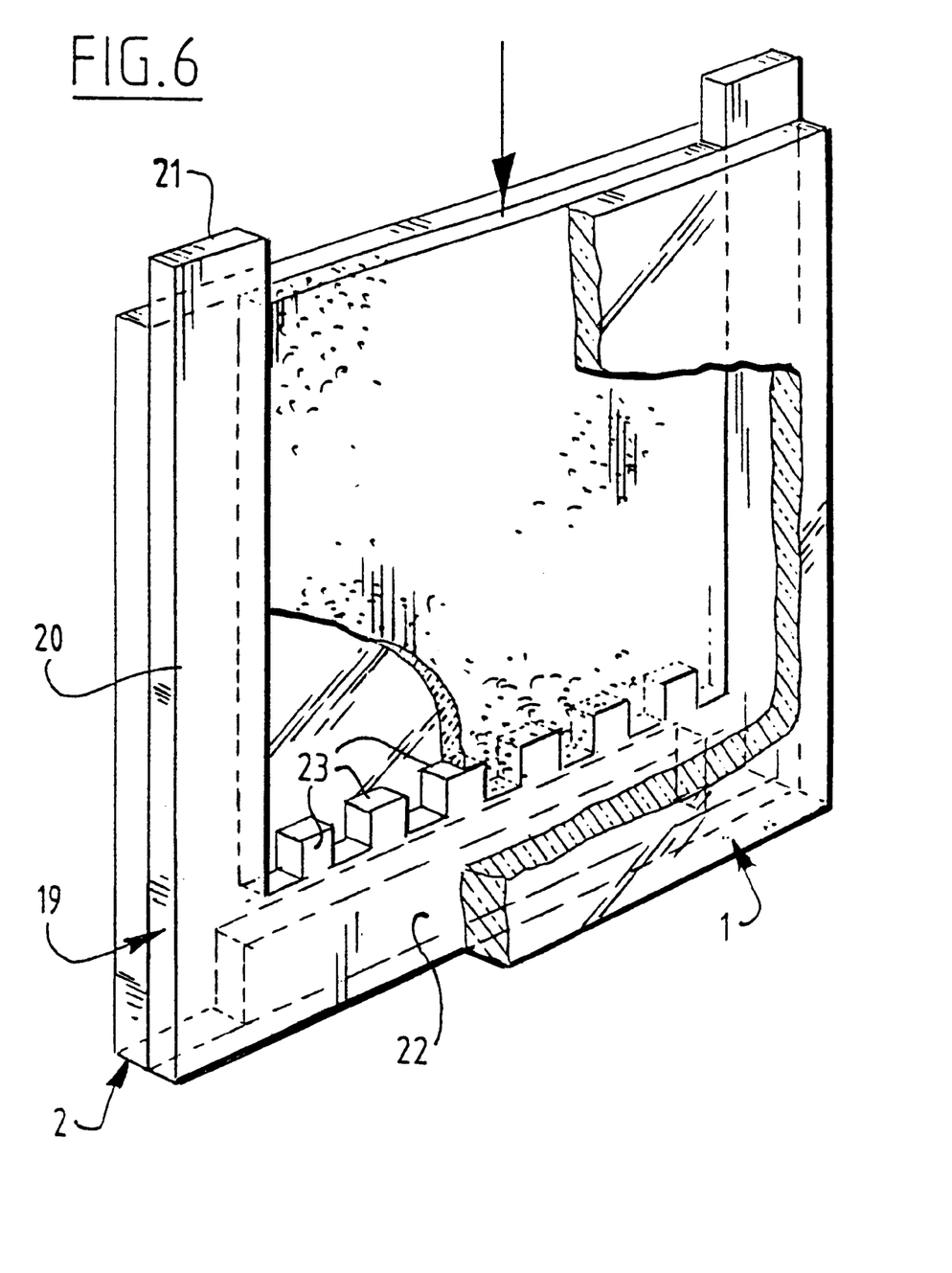
FIG. 6 shows a partly broken away perspective view of a second embodiment of a gel cassette according to the invention placed upside down.
Figure 7:
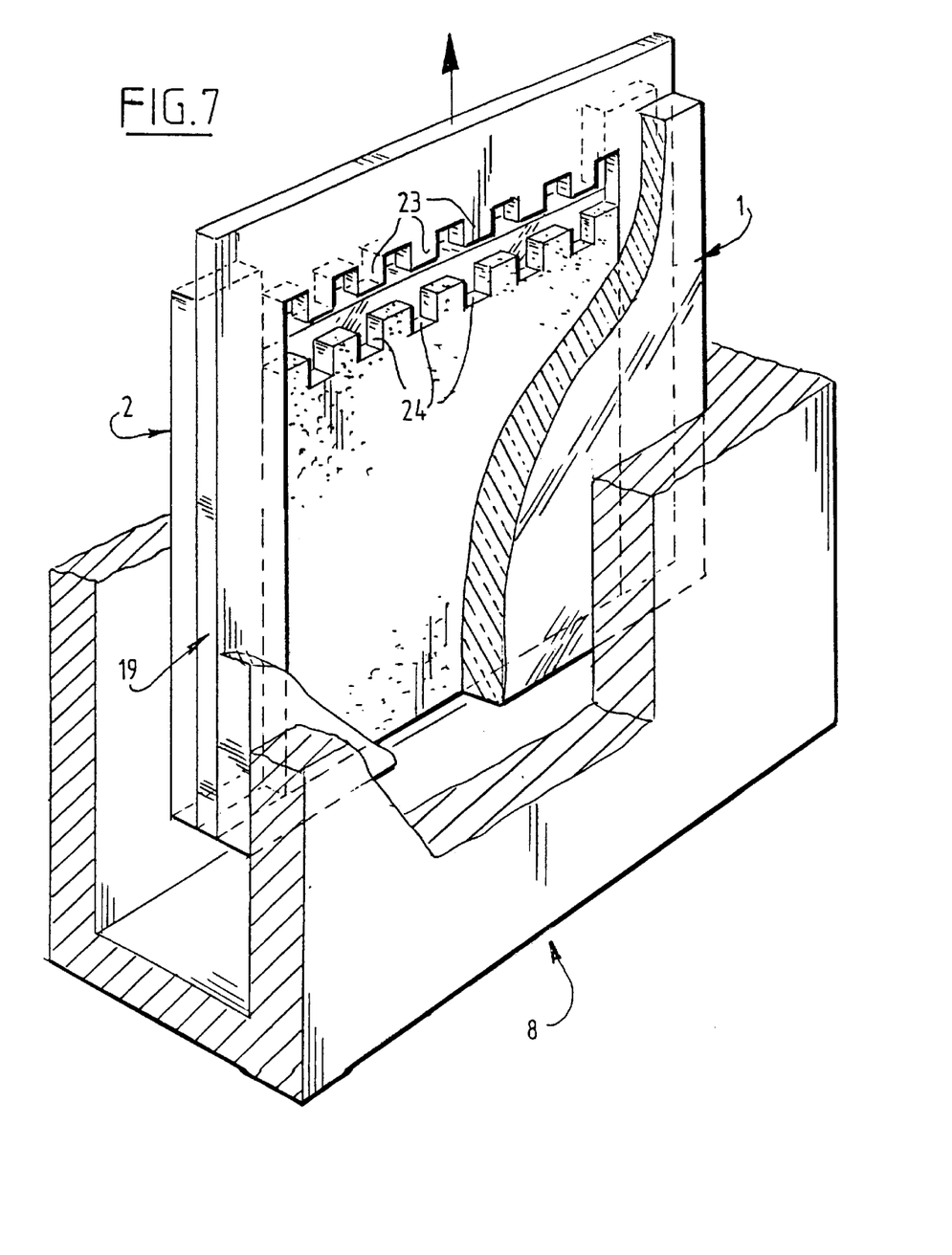
FIG. 7 shows a partly broken away perspective view of a gel cassette as shown in FIG. 6 placed in an electrophoresis apparatus.

FIGS. 6 and 7 show an alternative embodiment of the spacer according to the invention. FIG. 6 shows a gel cassette consisting of glass plates 1 and 2 between which is received a U-shaped spacer 19. The spacer 19 consists of the vertical parts 20 and a horizontal comb part 22 which is provided with teeth 23. After casting and polymerization of the gel, the comb can be removed from the gel by means of pushing using the protruding portions 21. This embodiment of the spacer can optionally have an H-shape. In that case the protruding portions 21 are situated on the other side of the spacer. The advantage hereof is that, when the gel cassette is turned over to its position of use, the comb 22 can be pulled out of the gel while the cassette is situated in the electrophoresis apparatus filled with buffer. The freed slots will immediately fill with buffer whereby accumulation of gas in the slots is prevented. Syringing the slots in order to remove air bubbles is then no longer necessary. This embodiment is not shown here.

FIG. 7 shows the position of use of this embodiment of the invention. The gel cassette is here placed in a buffer container 8 and it can clearly be seen how the teeth 23 of the comb of the spacer leave behind slots 24 for placing therein of samples.

Figure 8:
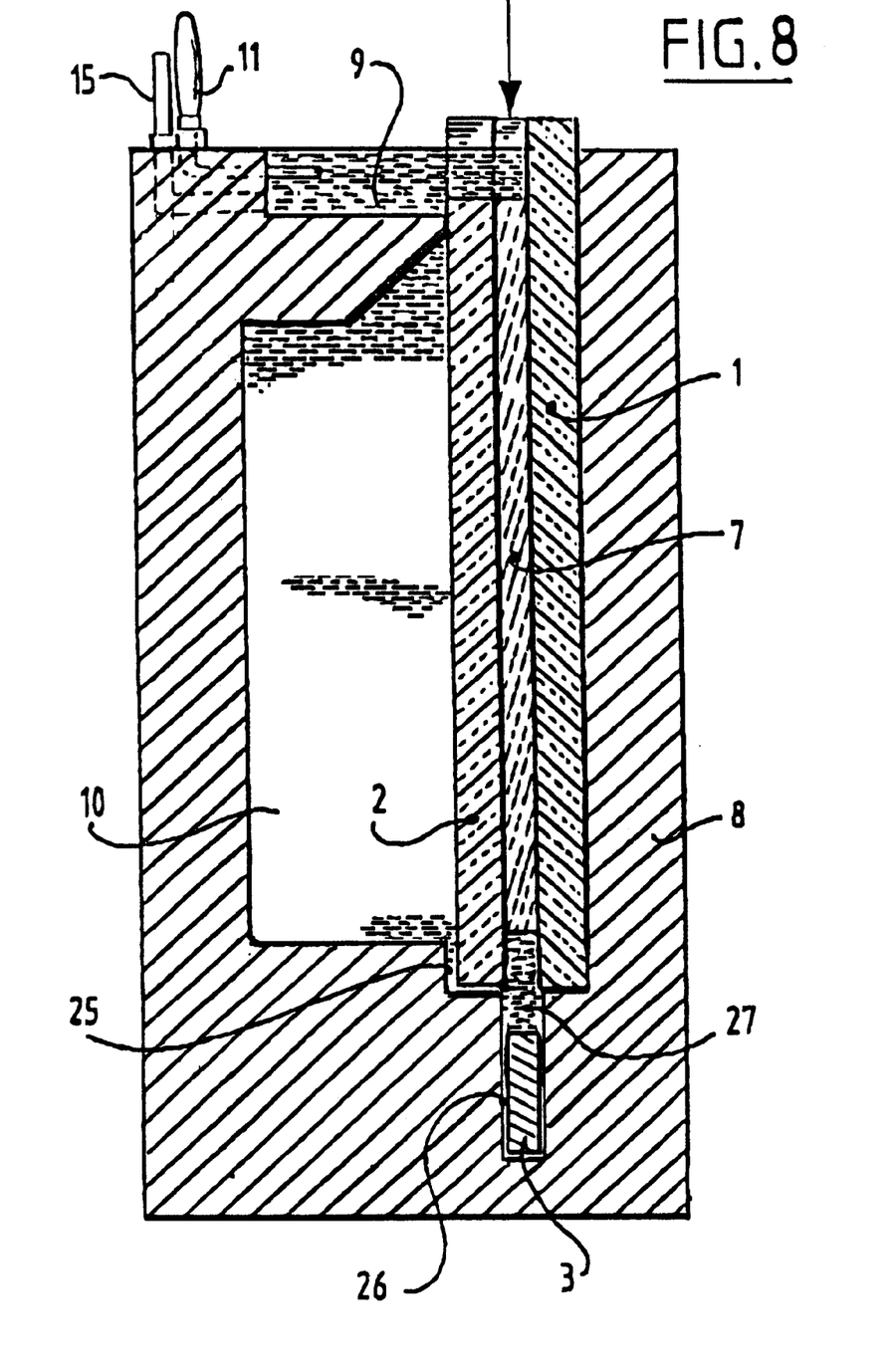
FIG. 8 shows a cross-sectional view of an alternative embodiment of an electrophoresis apparatus according to the invention.

FIG. 8 shows an alternative embodiment of the electrophoresis apparatus with which gas accumulation under the gel can be prevented. The gel cassette consisting of the glass plates 1 and 2 and the gel 7 is situated in a recess in the bottom of the buffer container. Under the gel and glass plate 2 is created a space 27 which is in contact with buffer compartment 10 via the passage 25 running under glass plate 2. A recess 26 is arranged under the space 27 for receiving the spacer 3. As soon as the gel cassette is placed in the buffer container and the spacer 3 is pushed into recess 25, the space 27 will fill with buffer via the passage 25. No gas can hereby accumulate under the gel since air bubbles cannot move to space 27 via the passage under the glass plate.

Figure 9:
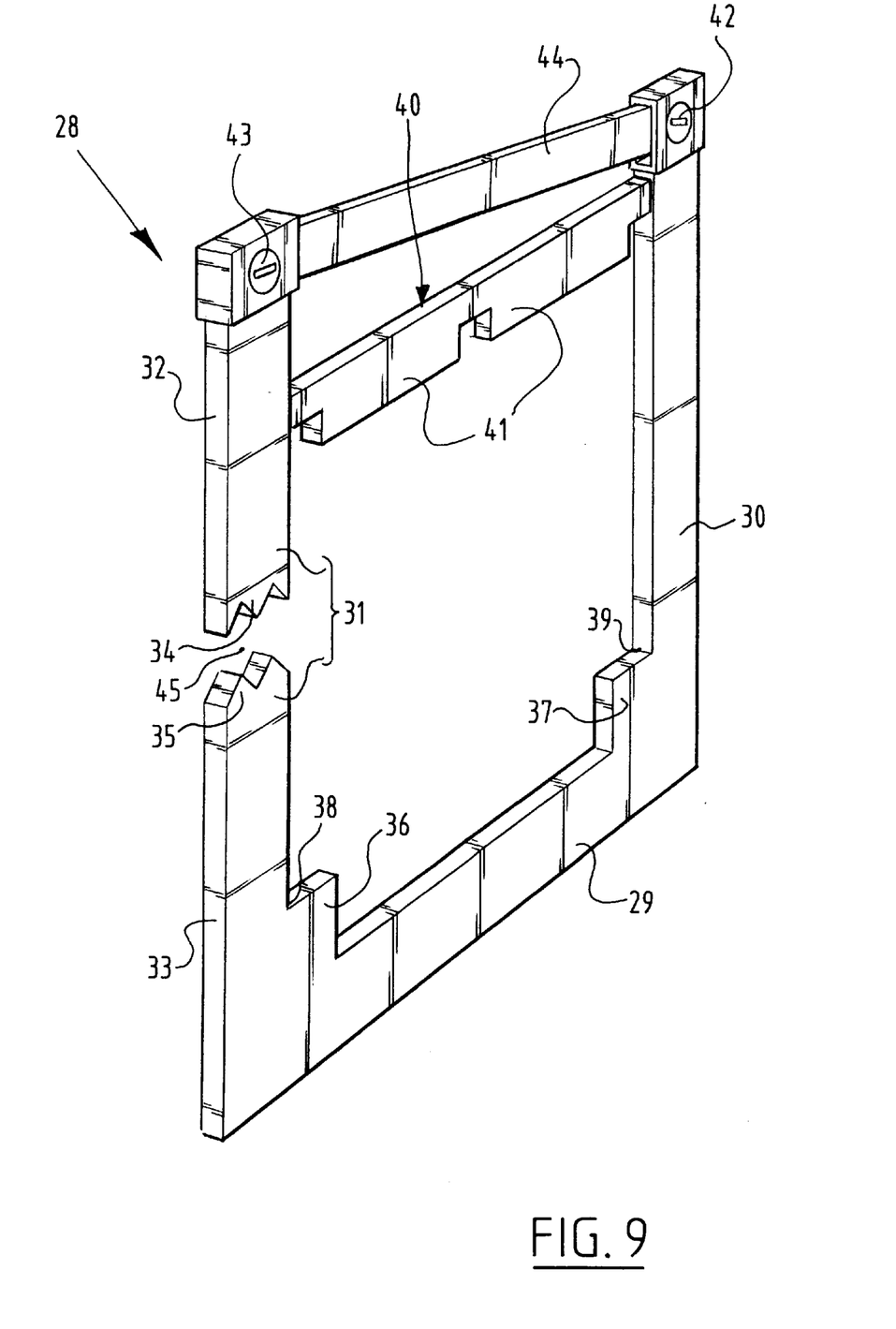
FIG. 9 shows a perspective view of a spacer which is suitable for casting perpendicular gels.

In FIG. 9 is shown an alternative embodiment of the spacer according to the invention with which so-called perpendicular gels can be cast. The spacer 28 consists of a base 29 and two vertical parts 30 and 31. Part 31 consists of two portions 32 and 33, which can be made into a whole via mutually fitting teeth 34 and 35. Pushed apart they define a passage opening 45 for gel solution. At the join between the horizontal base 29 and the vertical parts 30 and 31 are situated shoulders 36 and 37 which can be used to capture in corners 38 and 39 air bubbles which may be present on the underside of a newly cast gel. The separate comb 40 shown here contains two wide teeth 41 and is suitable for casting two perpendicular gels. The upper ends of the vertical parts 30 and 31 are hingedly connected to both ends of a connecting bridge 44 by means of hinge points 42 and 43. The connecting bridge facilitates handling of the two separate components.

A spacer 28 as shown in FIG. 9 is used to cast perpendicular gels, wherein the gradient runs in horizontal direction. In order to cast such gels the gel cassette, optionally together with the electrophoresis apparatus when casting takes place in this apparatus, is turned 90° whereby the passage opening of the spacer is situated at the top. The gel can subsequently be cast via this opening. When the cassette is already placed in the electrophoresis apparatus prior to casting, it must be provided on its side with an opening for passage of the gel solution (not shown).

Figure 10:
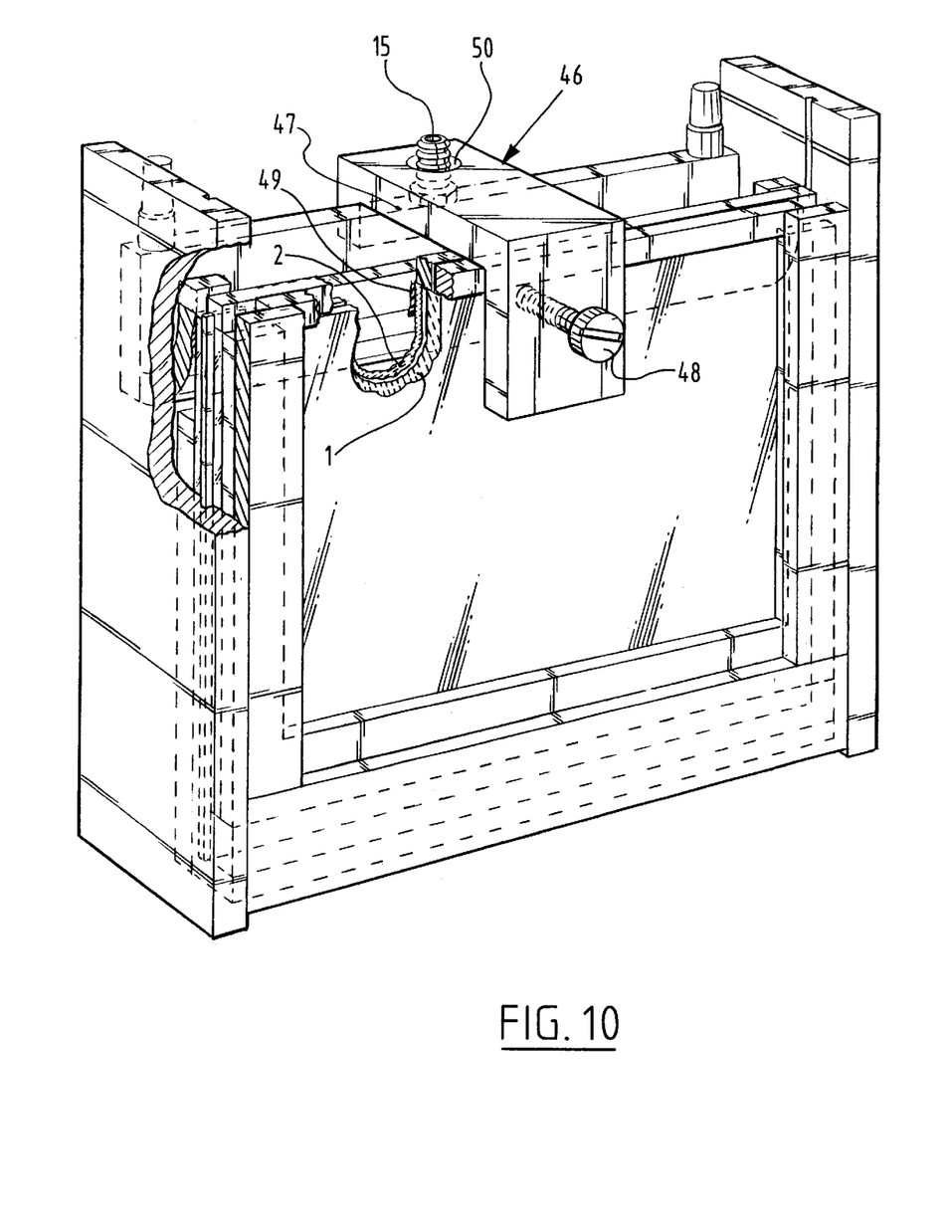
FIG. 10 is a perspective view of an electrophoresis apparatus according to the invention having placed therein gel cassette with pressure clamp for use in casting perpendicular gels.
Figure 11:
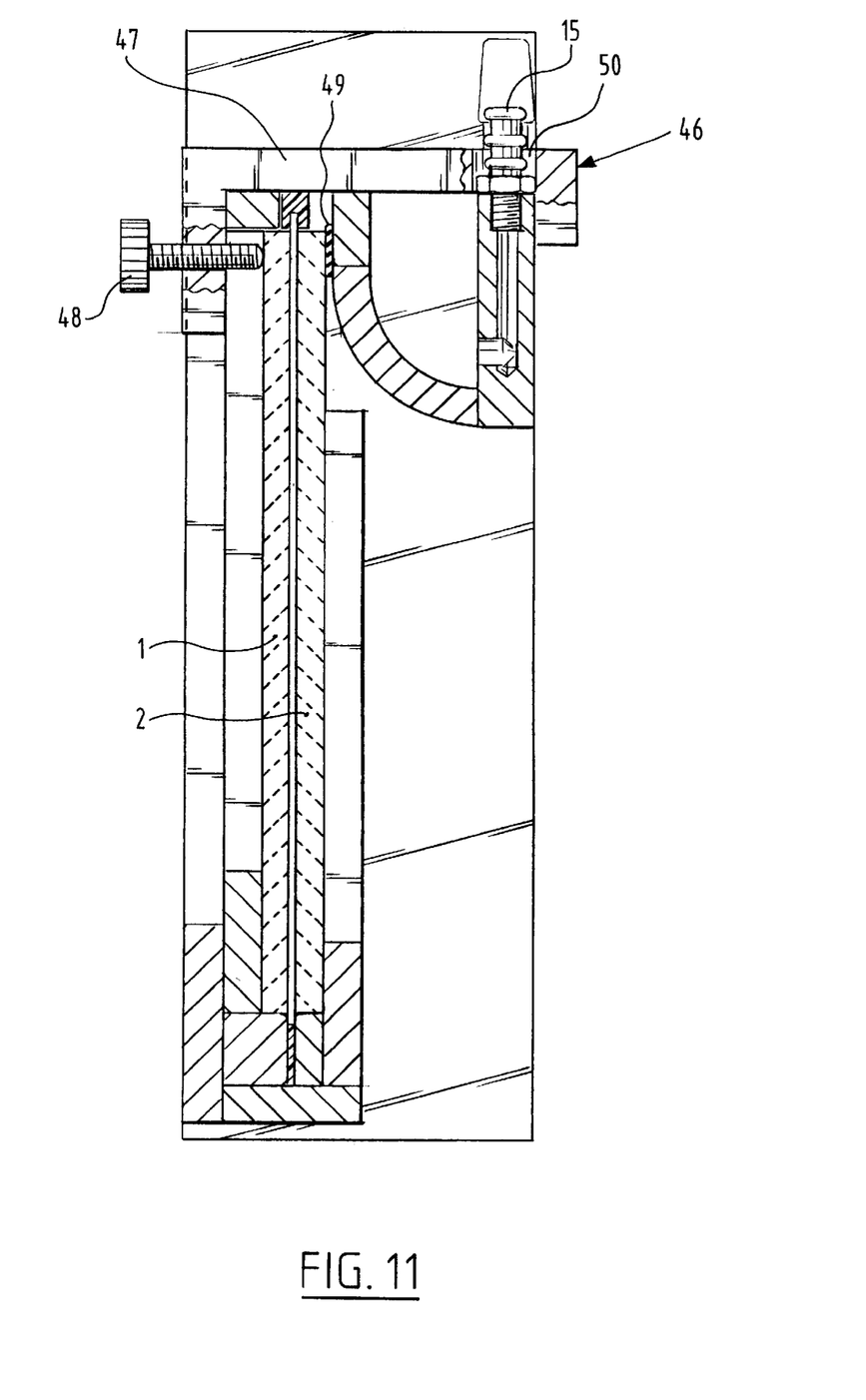
FIG. 11 shows a cross-section of the electrophoresis apparatus of FIG. 10.

FIGS. 10 and 11 show in perspective and in cross-section the use of the pressure clamp 46 which consists of a U-shaped element 47, through one of the legs of which is inserted a screw 48 for pressing glass plates 1 and 2 against a rubber seal 49. The clamp further has a recess 50 for passage of the so-called hose pillar 15. The clamp is hereby fixed.

Figure 12A:
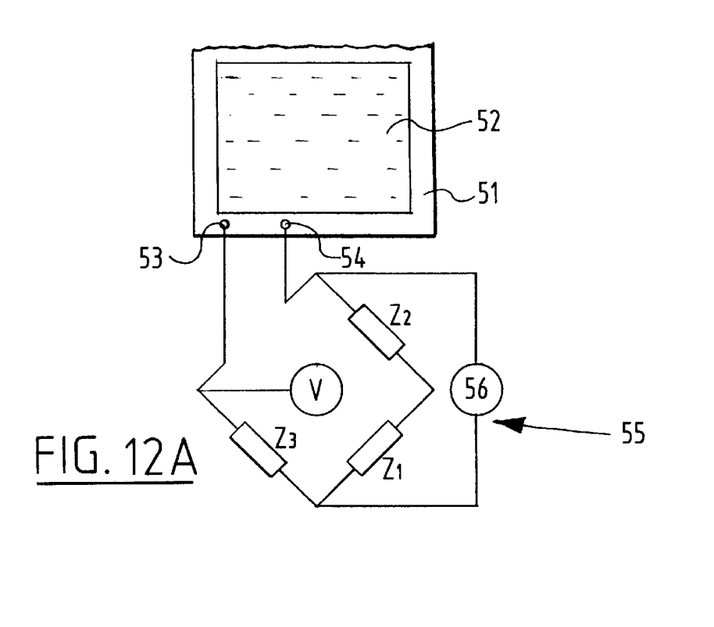
FIG. 12A is a schematic view of an apparatus for determining the electrical conductance of the electrophoresis buffer.
Figure 12B:
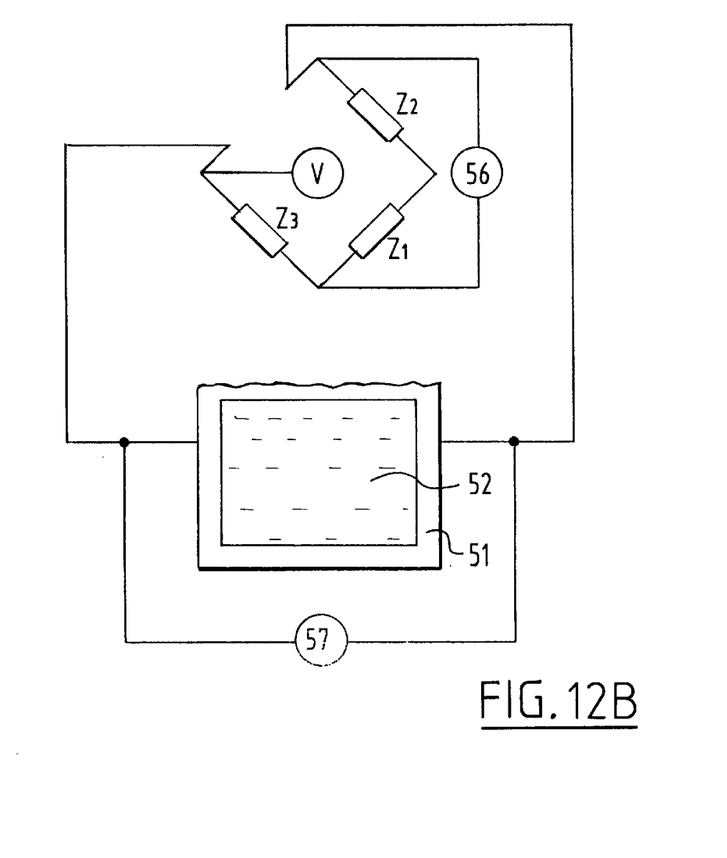
FIG. 12B is a schematic view of an apparatus for simultaneously determining the electrical conductance of the electrophoresis buffer and the effective electrical field strength in the gel.

FIGS. 12A and 12B show schematically the means respectively for determining the electrical conductance of the buffer and for determining both the conductance of the buffer and the field strength in the gel.

Situated in a gel tray 51 in which a gel 52 is placed are two sensors 53 and 54, between which the resistance is measured by means of an alternating current bridge 55. The bridge is connected to an external alternating current source 56. The bridge is in equilibrium when:

$Z_2 \times Z_1 = Z_3 \times (\text{resistance buffer})$

V then equals 0. The resistances $Z_1$, $Z_2$ and $Z_3$ are for instance chosen such that the bridge is in equilibrium when the buffer is fresh. When the conductance of the buffer changes the resistance will also change. As soon as V assumes a predetermined value the indicator means (not shown) will give the user a sign that the buffer needs replacing.

In FIG. 12B the alternating current bridge is connected in similar manner over the electrodes, symbolized by voltage source 57, which provides the constant voltage at which the electrophoresis is carried out. In this way the effective electrical field strength in the gel as well as the conductance of the buffer can be determined.

The gel cassette and electrophoresis apparatus according to the invention have a number of advantages. In the first place it becomes possible to assemble a leak-free gel cassette in simple manner. The embodiment with the built-in comb has the added advantage that a separate comb is no longer necessary. The total casting process can now be completed with a single component.

The measuring points in one or both glass plates make it possible to follow different gel parameters, such as electrical field and temperature development, during the electrophoresis. When these parameters are recorded their possible effect on the produced gel can be determined later. It is conceivable to later correct, for instance by means of a computer, a gel pattern of a gel of which the lines of flux do not run horizontally but which display so-called "smiling".

The flushing conduit of the new electrophoresis apparatus according to the invention has a dual effect, that is, the removal of the air bubbles under the gel and flushing of the buffer liquid, whereby exhaustion is prevented. In an advanced embodiment the electrophoresis apparatus according to the invention is provided with means for measuring, recording and processing the gel parameters detected via the measuring points.

What is claimed is:

1. A gel cassette comprising two glass plates and a one piece, continuous, substantially H- or U-shaped spacer placed between and in contact with the two glass plates, which spacer is movable between a first position for casting of the gel and a second position for use in electrophoresis.

2. The gel cassette as claimed in claim 1 wherein one of the two glass plates is provided with sensors which contact the gel for measuring at least one gel parameter.

3. The gel cassette as claimed in claim 2 wherein the gel parameter is potential.

4. The gel cassette as claimed in claim 2 wherein the gel parameter is temperature.

5. The gel cassette as claimed in claim 1 wherein the spacer consists of two spaced substantially vertical parts that are mutually connected by a substantially horizontal part substantially perpendicular to the vertical parts.

6. The gel cassette as claimed in claim 5 wherein the horizontal part is provided with teeth.

7. The gel cassette as claimed in claim 1 wherein the spacer is manufactured from TEFLON.

8. A movable, one piece, continuous, substantially H- or U-shaped spacer comprising two spaced substantially vertical parts that are mutually connected by a substantially horizontal part substantially perpendicular to the vertical parts wherein the horizontal part is provided with teeth for use in the gel cassette as claimed in claim 1.

9. The spacer as claimed in claim 8 wherein the spacer comprises TEFLON.

10. The spacer as claimed in claim 8 wherein the vertical parts are wider on their outer end remote from the horizontal part.

11. The spacer as claimed in claim 8 wherein the outward directed edge of the vertical spacer parts runs straight while the inward directed edge tapers toward the outer end in a convex, concave, or linear manner.

12. The spacer as claimed in claim 8 wherein at least one of the vertical parts consists of two portions which connect mutually in liquid-tight manner to define a passage opening for gel solution.

13. The spacer as claimed in claim 8 further comprising a shoulder at the position of the connection of the horizontal part onto the vertical part.

14. An assembly of a gel cassette as claimed in claim 1 and an electrophoresis apparatus comprising a buffer container consisting of an upper buffer compartment and a lower buffer compartment, power points for applying a voltage between the upper buffer compartment and the lower buffer compartment, and means for preventing gas accumulation beneath the gel cassette placed in the apparatus.

15. An adapter set for casting perpendicular gels comprising a pressure clamp consisting of a U-shaped element and a pressure element protruding through one of the legs thereof, and a spacer as claimed in claim 8.

16. The adapter set as claimed in claim 15 further comprising a recess incorporated in the U-shaped element for passage of a hose pillar of a buffer container.

17. An electrophoresis gel cassette comprising two glass plates and a one piece, continuous, substantially H- or U-shaped spacer placed between and in contact with the two glass plates, which spacer is movable between a first position for casting of a gel and a second position for use in electrophoresis and wherein one glass plate has sensors attached thereto which contact the gel for measuring one or more gel parameters.

18. The electrophoresis gel cassette as claimed in claim 17 wherein the sensors are temperature-sensitive resistances.

19. The electrophoresis gel cassette as claimed in claim 17 wherein the sensors are electrically conducting.

20. The electrophoresis gel cassette as claimed in claim 17 wherein the sensors comprise platinum.

21. An electrophoresis apparatus comprising a buffer container having an upper buffer compartment and a lower buffer compartment, power points for applying a voltage between the upper buffer compartment and the lower buffer compartment, and means for preventing gas accumulation beneath a gel cassette placed in the apparatus, wherein the means for preventing gas accumulation is one of integral means for flushing a remaining space between glass plates of the gel cassette under the gel, and a recess situated in the bottom of the lower buffer compartment for partly receiving therein a gel cassette having glass plates, which recess defines a space between the gel cassette placed in the apparatus, which space is in contact with the lower buffer compartment via a passage under one of the glass plates.

22. The electrophoresis apparatus as claimed in claim 21 wherein the means for flushing take the form of a conduit with a plurality of outlet openings.

23. The electrophoresis apparatus as claimed in claim 21 further comprising means for measuring gel parameters detected by sensors in one of the glass plates of the gel cassette.

24. The electrophoresis apparatus as claimed in claim 21 further comprising means for determining the electrical conductance of the buffer, the effective electrical field strength in the gel, or both.

25. The electrophoresis apparatus as claimed in claim 24 further comprising indicator means coupled to the determining means for indicating when the buffer is exhausted, what the effective field strength is, or both.

* * * * *